United States Patent [19]
Phillips et al.

[11] Patent Number: 5,973,178
[45] Date of Patent: Oct. 26, 1999

[54] DYE INTERMEDIATES

[75] Inventors: Thomas S. Phillips, North Providence, R.I.; Ronald P. Pedemonte, Vockenhausen-Eppstein, Germany

[73] Assignee: DyStar L.P., Charlotte, N.C.

[21] Appl. No.: 09/077,217

[22] PCT Filed: Oct. 4, 1996

[86] PCT No.: PCT/US96/15973

§ 371 Date: May 20, 1998

§ 102(e) Date: May 20, 1998

[87] PCT Pub. No.: WO97/19047

PCT Pub. Date: May 29, 1997

Related U.S. Application Data

[60] Provisional application No. 60/007,496, Nov. 22, 1995.

[51] Int. Cl.⁶ .................................................. C07C 305/12
[52] U.S. Cl. ............................ 558/34; 558/51; 558/184; 560/254; 560/308; 564/440
[58] Field of Search .................. 558/31, 34, 51, 558/184; 560/254, 308; 564/440

[56] References Cited

U.S. PATENT DOCUMENTS 3,301,884  1/1967  Meininger et al. ...................... 260/453
5,155,271  10/1992  Aeschlimann et al. ................. 564/176

OTHER PUBLICATIONS

The Merck Index, 11ᵗʰ Edition, "An Encyclopedia of Chemicals, Drugs, and Biologicals", Edited by S. Budavari, Rahway, NJ: Merck & Co., Inc., 1989, No. 510 (p. 81). No. 3100 (p. 491).

*Primary Examiner*—Johann Richter
*Assistant Examiner*—John F. Dolan
*Attorney, Agent, or Firm*—Connolly & Hutz

[57] ABSTRACT

A compound of the formula:

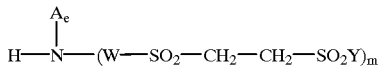

wherein:
A is hydrogen, a substituted or unsubstituted $C_1$ to $C_4$ alkyl, a substituted or unsubstituted $C_1$ to $C_4$ alkoxy or a substituted or unsubstituted phenyl;

W is a substituted or unsubstituted phenylene or a substituted or unsubstituted naphthylene;

Y is —$CH_2$—$CH_2$—Z wherein Z is selected from —$OSO_3H$, —$SSO_3H$, —$OPO_3H$, —$OCOCH_2$—$Cll_3$, Cl, Br or F; and m is 1 or 2, e is 0 or 1,
with the sum of e+m=2.

1 Claim, No Drawings

DYE INTERMEDIATES

CROSS REFERENCE TO RELATED APPLICATION

This application claims the benefit of U.S. Provisional Patent Application No. 60/007,496 filed Nov. 22, 1995, and is a 371 of PCT/US96/15973 filed Oct. 4, 1996.

BACKGROUND OF THE INVENTION

TECHNICAL FIELD

This invention is directed to the field of fiber reactive dye intermediates useful in the preparation of fiber reactive dyes. Fiber reactive dyes containing the reactive vinyl sulfone moiety are well known; see e.g. U.S. Pat. No. 2,657,205. The vinyl sulfone moiety may be represented by the formula: —$SO_2$—CH=$CH_2$. The vinyl group forms a covalent bond with pendant hydroxy or amine groups in the substrate which is to be dyed yielding dyeing of exceptional fastness.

Generally, the vinyl sulfone group is incorporated into the dye molecule by forming an amine containing at one least one vinyl sulfone group. The amine is then diazotized and coupled with a coupling component to form the dyestuff or it may be condensed with a dyestuff containing labile halogen moiety. Fiber reactive dyes containing the vinyl sulfone moiety such as monoazo, disazo, polyazo dyes, their metal complexes, the anthraquinone dyes, the phthalocyanine dyes, the formazan dyes and the dioxazine dyes are well known.

SUMMARY OF THE INVENTION

This invention is that of a new dye intermediate of the formula:

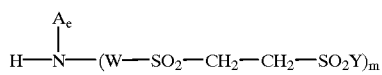

wherein:
  A is selected from hydrogen, a substituted or unsubstituted alkyl of 1 to 4 carbon atoms, a substituted or unsubstituted alkoxy of 1 to 4 carbons, or a substituted or unsubstituted phenyl;
  W is selected from substituted and unsubstituted phenylene and naphthylene;
  Y is —CH=$CH_2$ or —$CH_2$—$CH_2$—Z wherein Z is selected from —$OSO_3H$, —$OCOCH_3$, —$OPO_3H$, —Cl and
  m and e are independently select from 0,1,2 with the sum of e+m=2.

DESCRIPTION OF THE PREFERRED EMBODIMENTS

The dye intermediates of this invention have the formula:

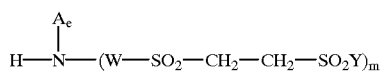

wherein:
  A is selected from hydrogen, a substituted and unsubstituted and unsubstituted $C_1$ to $C_4$ alkyl, a substituted and unsubstituted $C_1$ to $C_4$ alkoxy and a substituted or unsubstituted phenyl;
  W is selected from substituted and unsubstituted phenylene and naphthylene;
  Y is selected from —$CH_2$—$CH_2$—Z wherein Z is selected from —$OSO_3H$, —$SSO_3H$, —$OPO_3H$, —$OCOCH_2$—$CH_3$, Cl, Br, F;
  preferably the —$OSO_3$—H group.
  m and e are independently select from 0,1,2 with the sum of e+m=2.

The moiety A may be substituted with one or more substituents such as —$SO_3H$, —COOH, cyano, hydroxy, sulfamoyl, halogen (Cl, F, Br), ethoxy, methoxy and the like, preferably A is methyl or hydrogen, most preferably hydrogen. Similarly, the moiety W may be substituted with one or more substituents such as sulfo, carboxy, hydroxy, halogen, cyano, cyanamid, methyl, ethyl, propyl, methoxy, ethoxy, propoxy; preferably W is phenylene substituted with at least one sulfo group. The dye intermediates of this invention are shown herein in their free acid form but it is apparent to one of ordinary skill in the art that they can and are useable in their free acid and soluble salt forms.

The dye intermediates of this invention can be used to prepare fiber reactive dyes by known methods. The term fiber reactive dyes is intended to mean dyes that are capable of forming a covalent bond with the substrate that is being dyed; e.g. by reacting with the hydroxyl group of a cellulosic fiber or with the reactive groups in natural and synthetic polyamides. These fiber reactive dyes may be represented by the general formula:

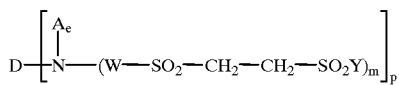

wherein:
  D represents a radical of dye such as a monoazo, disazo, polyazo dye or a metal complex thereof or anthraquinone, phthalocyanine, formazan or dioxazine dye;
  P is an integer of 1 to 3, preferably 1 or 2; and the term A, W, Y, m and e are as defined above.

The new dye intermediates of the invention may be prepared from vinyl sulfone substituted phenylamine or naphthylamine. The amine moiety is first acylated using an acyl anhydride or acid chloride; preferably the amine moiety is acetylated using acetic anhydride. The acylated, vinyl sulfone substituted amine is then reacted with an equimolar amount of mercaptoethanol. The resulting sulfide compound is then oxidized using an oxidizing agent such as hydrogen peroxide in the presence of a catalyst such as sodium tungstate to yield the sulfone having the general formula: AR—$SO_2$—$(CH_2)_2$—$SO_2$—$(CH_2)_2OH$; wherein "AR" is a phenyl or naphthyl amide. The amide is deacylated and esterified, preferably the esterification is done in sulfuric acid to yield the sulfato ester.

The following examples illustrate the preparation of dye intermediates according to the invention:

EXAMPLE 1

1-Aminobenzene-3-(2-(2-sulfatoethyl)sulfonyl) ethylsulfone:

285 parts of 1-aminobenzene-3-(2-sulfatoethyl)sulfone was acetylated with 107 parts of acetic anhydride in an aqueous medium at 20–30° C. The acetylated product was reacted with 80.5 parts of 2-mercaptoethanol at pH 8.0–9.0. The resulting sulfide product was oxidized to the sulfone with 160 parts of 30% hydrogen peroxide and 2 parts sodium tungstate at pH 6–7 and 50–60° C. The sulfone product was deacetylated by lowering the pH of the reaction mixture to <1 with 37% hydrochloric acid and heating to 95–100° C. When complete, the reaction was cooled to 20–25° C. and the pH adjusted to 4–4.5 with 50% sodium hydroxide. The amine was isolated by filtration and the presscake rinsed with 200—400 parts water. The product was dried in a vacuum oven to afford 277 parts of 1-aminobenzene-3-(2-hydroxyethyl) sulfonyl)ethylsulfone. For the esterification, the dried hydroxy product was added portion wise to 1000 parts of monohydrate at 40–50° C. When complete, the esterified product was separated by drowning the reaction mixture slowly in to ice/water and isolated by filtration. Drying in a vacuum oven afforded 280 parts (75% yield) of 1-aminobenzene-3-(2-(2-sulfatoethyl)sulfonyl)ethylsulfone.

EXAMPLE 2

1-Aminobenzene-4-(2-(2-sulfatoethyl)sulfonyl) ethylsulfone:

This product was prepared substantially in accordance with the procedure set forth in Example 1, except that 1-aminobenzene-4-(2-sulfatoethyl)sulfone was used in place of 1-aminobenzene-3-(2-sulfatoethyl) sulfone.

The following examples illustrate the use of the new dye intermediates of this invention in various fiber reactive dyes. These dyes may be prepared by methods well known in the art by reacting typical precursors for a particular dye type wherein one or more of the precursors contains the new dye intermediates of this invention.

Monoazo and disazo fiber reactive dyes in which the dye intermediate of the invention is incorporated into the dye molecule as a diazonium component for the dye follow.

Monoazo Dyes

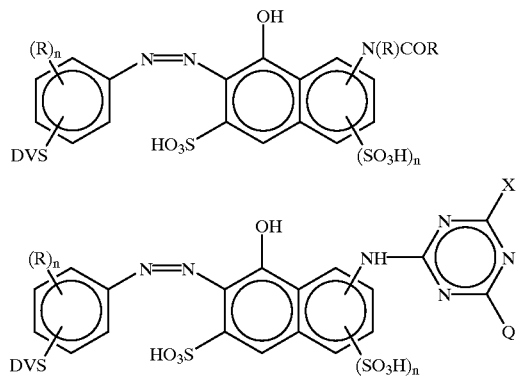

Diazo Dyes

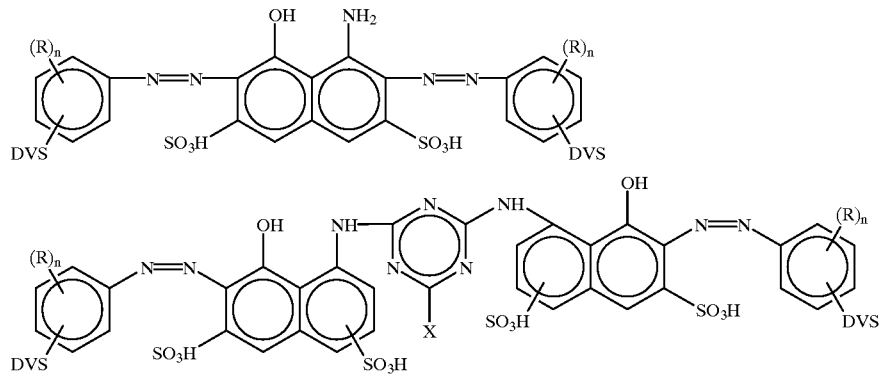

wherein:

DVS is $-SO_2-C_2H_4-SO_2-C_2H_4OSO_3H$;

n is independently selected from 1 and 2;

R is independently selected from H. substituted or unsubstituted $C_1$ to $C_4$ alkyl, a substituted or unsubstituted $C_1$ to $C_4$ alkoxy, a substituted or unsubstituted phenyl and sulfo; suitable substituents are sulfo, carboxy, hydroxy, halogen, cyano, cyanamid, methyl, ethyl, propyl, methoxy, ethoxy, and propoxy;

X is independently selected from Cl, F, OH, NHCN and Q;

Q is independently selected from:

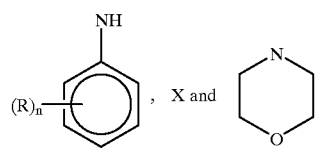, X and

The fiber reactive dye intermediate of this invention may also be incorporated into a dye molecule as a substituent of an s-triazine moiety wherein the s-triazine moiety is attached to a monoazo dye, a disazo dye, a metal complex of a monoazo or disazo dye, an anthraquinone dye, or triphendioxazine dye.

Exemplary dyes in which the dye intermediate is incorporated into the dye molecule through an s-triazine moiety follow.
Monoazo Dyes
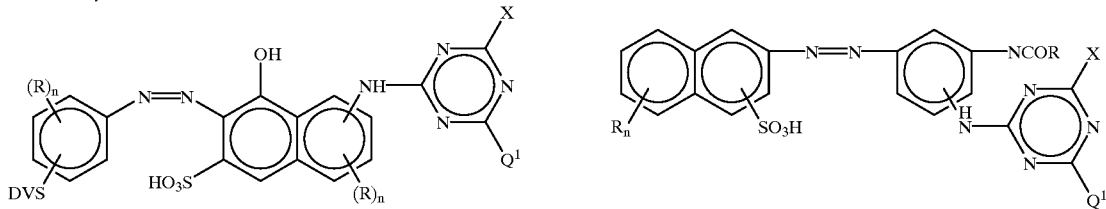
Diazo Dyes
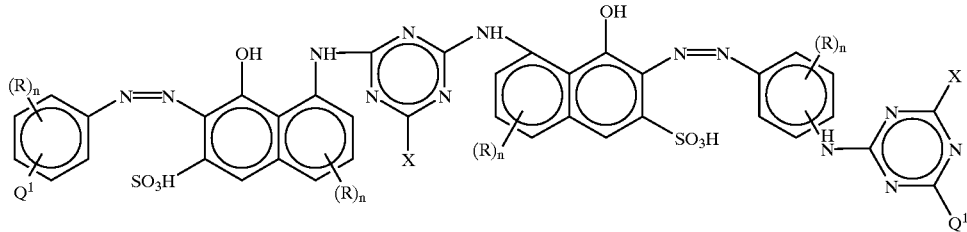
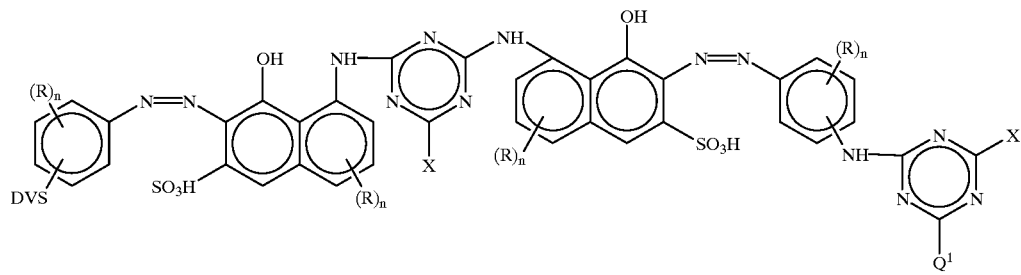
Metal Complexed Monoazo Dyes
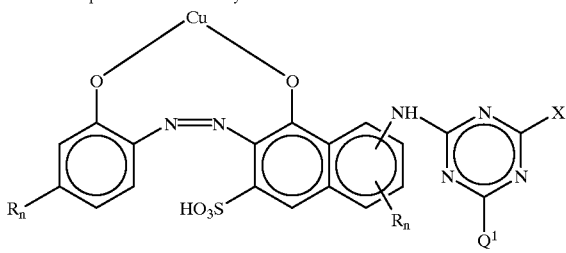
Triphendioxazine Dyes
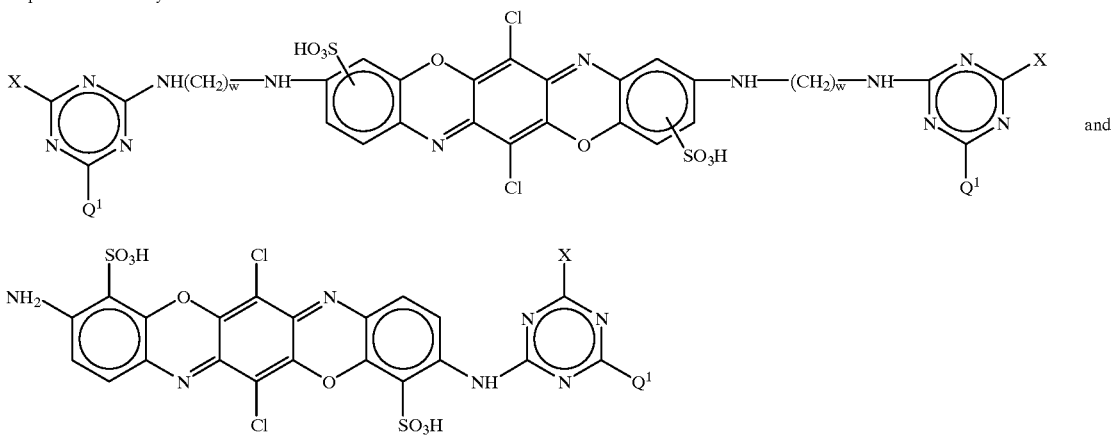
and Anthraquinone Dyes

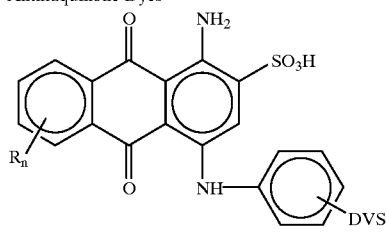

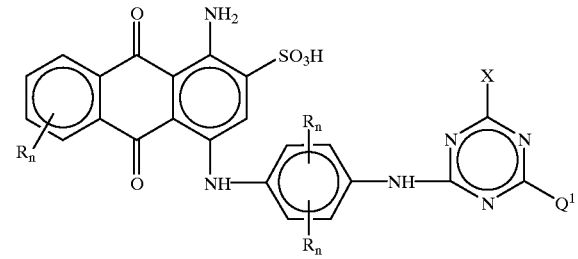

Phthalocyanine Dyes

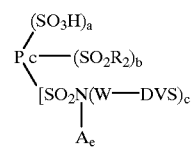

In the above formulae the following meanings are intended:

DVS is $-SO_2-C_2H_4-SO_2-C_2H_4OSO_3H$;

A and e are as defined above;

R is independently selected from H, substituted or unsubstituted $C_1$ to $C_4$ alkyl, a substituted or unsubstituted $C_1$ to $C_4$ alkoxy, a substituted or unsubstituted phenyl and sulfo; suitable substituents are sulfo, carboxy, hydroxy, halogen, cyano, cyanamid, methyl, ethyl, propyl, methoxy, ethoxy, and propoxy;

n is independently selected from 1 and 2;

X is independently selected from Cl, F, OH, NHCN and $Q^1$;

Q is 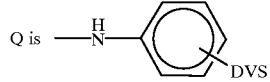

Pc is the radical of a copper or nickel phthalocyanine, $R_2$ is an amino group of the formula $-NR^2R^3$, in which $R^2$ and $R^3$ independently of one another are hydrogen or alkyl having 1 to 4 carbon atoms, which can be substituted by hydroxyl or sulfo, or is a heterocyclic N-containing radical, such as the morpholine or piperidino radical;

W is selected from phenylene and naphthylene;

a is a number from 2 to 3;

b is a number from zero to 3 and c is a number from 1 to 2, the sum of (a+b+c) being a number from 3 to 4.

Formazan Dyes

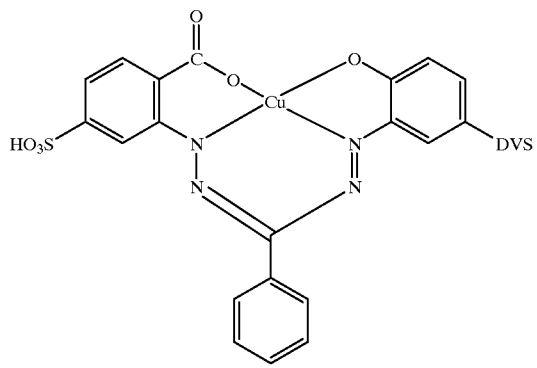

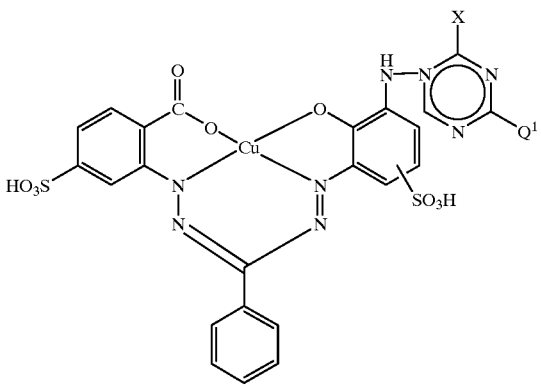

wherein DVS and $Q^1$ are defined above.

The dyes containing a fiber reactive intermediate according to the invention are useful, as water-soluble dyestuffs, for coloring (dyeing and printing) of fibers, leather or other materials containing hydroxy groups and/or amino groups. They may be used in their free acid form, as salts and in their vinylized form. Exemplary materials are natural, regenerated or synthetic, nitrogen-containing fibers and natural, regenerated or synthetic hydroxy group containing fibers. The dyestuffs according to the invention are capable of coloring these materials to deep, brilliant shades ranging from yellow to blue with superior fastness properties. The fiber-reactive groups in the dye intermediates of the invention can react with the amine and hydroxy groups of the material, such as a cotton (hydroxy groups), to form a covalent bond and thus form a bonded link with the fiber.

Typical nitrogen-containing synthetic materials useful in this invention are polyurethanes and polyamides such as nylon 6, nylon 6/6 and nylon 11. Typical natural polyamide materials are silk and wool and other animal hair products. Typical materials containing hydroxy groups are polyvinyl alcohols, cellulosic materials such as cotton, other vegetable fibers, such as linen, hemp, jute, and their regenerated products, such as viscose rayon or cuprammonium rayon.

The compounds prepared from the novel dye intermediates of the invention can be applied by known application techniques for fiber-reactive dyestuffs. In general, a procedure is followed in which an aqueous solution of the compounds or their metal complex are applied to the materials, optionally in the presence of a thickener and/or other auxiliaries to improve the affinity, leveling and migration properties. After application, the dye is fixed to the fiber to form a covalent bond therewith.

To those skilled in the art to which this invention relates many changes, modifications and widely different embodiments and application of the invention will suggest themselves without departing from the spirit and scope of the invention. The disclosure and the description herein are illustrative and are not intended to be limiting.

We claim:

1. A compound of the formula:

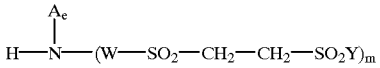

wherein:

A is hydrogen, a substituted or unsubstituted $C_1$ to $C_4$ alkyl, a substituted or unsubstituted $C_1$ to $C_4$ alkoxy or a substituted or unsubstituted phenyl;

W is a substituted or unsubstituted phenylene or a substituted or unsubstituted naphthylene;

Y is —$CH_2$—$CH_2$—Z wherein Z is selected from —$OSO_3H$, —$SSO_3H$, —$OPO_3H$, —$OCOCH_2$ —$CH_3$, Cl, Br or F; and m is 1 or 2, e is 0 or 1, with the sum of e+m=2.

* * * * *